United States Patent [19]

Woynar et al.

[11] Patent Number: 5,994,491
[45] Date of Patent: Nov. 30, 1999

[54] PROCESS FOR THE PRODUCTION OF POLYISOCYANATES HAVING A BIURET STRUCTURE

[75] Inventors: Helmut Woynar; Manfred Schmidt, both of Dormagen; Jürgen Grönen, Overath, all of Germany

[73] Assignee: Bayer Aktiengesellschaft, Leverkusen, Germany

[21] Appl. No.: 09/022,792

[22] Filed: Feb. 13, 1998

[30] Foreign Application Priority Data

Feb. 26, 1997 [DE] Germany .............................. 197 07 576

[51] Int. Cl.$^6$ ..................................................... C08G 18/32
[52] U.S. Cl. .............................................. 528/68; 560/335
[58] Field of Search ................................. 560/335; 528/68

[56] References Cited

U.S. PATENT DOCUMENTS

| 3,954,825 | 5/1976 | Touhey et al. | 560/335 |
| 4,264,519 | 4/1981 | Hennig et al. | 260/453 AB |
| 4,618,706 | 10/1986 | Scholl et al. | 560/335 |

*Primary Examiner*—Rachel Gorr
*Attorney, Agent, or Firm*—Joseph C. Gil; Noland J. Cheung

[57] ABSTRACT

A process for the production of polyisocyanates having a biuret structure, comprising continuously combining organic diisocyanates having aromatically attached isocyanate groups in a mixing chamber with organic diamines having aromatically attached amino groups in a molar ratio of at least 8:1 to form a reaction mixture; and reacting said reaction mixture at a temperature of above 180° C., wherein a residence time of said reaction mixture in the mixing chamber from when said organic diisocyanates and said organic diamines are combined is at most 60 seconds.

7 Claims, 1 Drawing Sheet

PROCESS FOR THE PRODUCTION OF POLYISOCYANATES HAVING A BIURET STRUCTURE

FIELD OF THE INVENTION

The present invention relates to a process for the production of polyisocyanates having a biuret structure by reacting excess quantities of organic diisocyanates having aromatically attached isocyanate groups with organic diamines at elevated temperatures. Such polyisocyanates may be used in the production of polyurethane plastics.

BACKGROUND OF THE INVENTION

It is known to produce polyisocyanates having a biuret structure by directly reacting excess quantities of organic diisocyanates with organic diamines at elevated temperatures. Thus, DE-OS 3,114,638 describes the reaction of excess quantities of a mixture of 80% 2,4- and 20% 2,6-diisocyanatotoluene with alkylphenylenediamines, wherein the reactants are reacted within a period of 3 hours at 100° C. with a zinc acetonyl acetate catalyst. While this approach, i.e., producing biurets with the addition of a catalyst, does indeed require only low temperatures, it would be preferable in practice, where possible, to avoid using a catalyst since, in order to terminate the reaction, the catalyst must then be inactivated with benzoyl chloride.

EP 0,003,505 describes an industrially practicable method for aliphatic isocyanates. In this process, the diamine is introduced into the initially introduced diisocyanate by means of a smooth jet nozzle of defined dimensions using elevated pressures. One disadvantage is that, when the described smooth jet nozzle is used with aromatic isocyanates under the conditions described in the Examples, it is not possible to suppress the formation of solids in the form of precipitated urea. For this reason, in the case of isocyanates, a urea dispersion is first purposefully produced in a preliminary stage at low temperatures of up to 120° C. so that it may subsequently be converted into the biurets by heating.

SUMMARY OF THE INVENTION

The present invention provides a process for the production of polyisocyanates having a biuret structure, comprising:

a) continuously combining organic diisocyanates having aromatically attached isocyanate groups in a mixing chamber with organic diamines having aromatically attached amino groups in a molar ratio of at least 8:1 to form a reaction mixture; and b) reacting said reaction mixture at a temperature of above 180° C., c) wherein a residence time of said reaction mixture in the mixing chamber from when said organic diisocyanates and said organic diamines are combined is at most 60 seconds.

Accordingly, the object of the present invention is to provide a single stage process for the production of polyisocyanates having a biuret structure based on isocyanates having aromatically attached isocyanate groups without unwanted solids formation occurring during the reaction of the isocyanates with organic diamines.

DETAILED DESCRIPTION OF THE INVENTION

Figure 1:
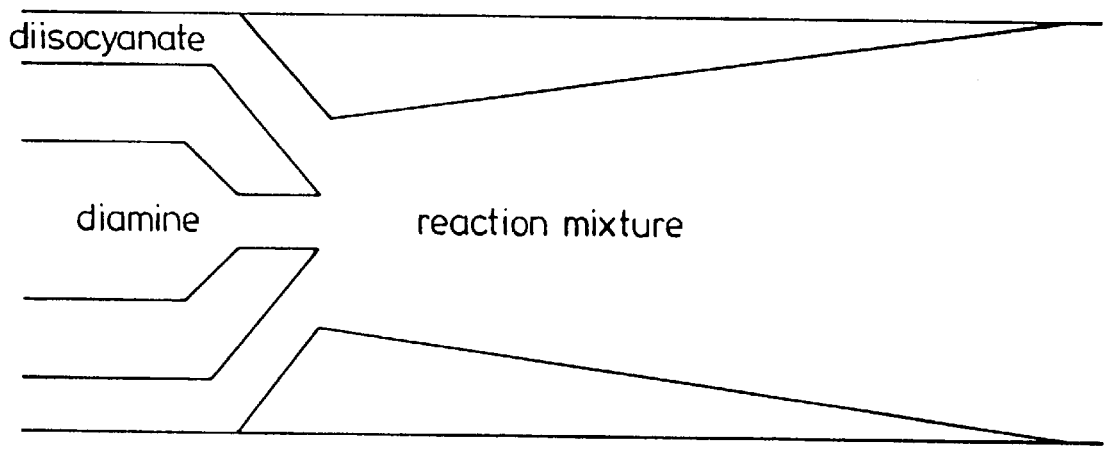
FIG. 1. Basic design of the mixing chamber

It has now surprisingly been found that it is possible to produce high quality polyisocyanates having a biuret structure based on aromatic diisocyanates or diamines, if the starting materials are reacted together at temperatures of above 180° C., preferably above 200° C., wherein the heat of reaction raises the temperature further to 220–270° C. This is extraordinarily surprising as it was hitherto thought that reaction temperatures of above 220° C. were to be avoided at all costs.

Starting materials for the process according to the present invention are organic diisocyanates having exclusively aromatically attached isocyanate groups and a molecular weight of below 300, such as, for example tolylene diisocyanates, preferably a mixture of 80 wt. % 2,4-tolylene diisocyanate and 20 wt. % 2,6-tolylene diisocyanate (TDI 80) or also preferably TDI 100 or TDI 65.

Further starting materials for the process according to the present invention are diphenylmethane diisocyanate, preferably diphenylmethane-4,4-diisocyanate.

Further starting materials for the process according to the present invention are organic diamines having organically attached amino groups and a molecular weight of below 300. 2,4-/2,6-Tolylenediamine or diphenylmethanediamines are preferred.

During the performance of the process according to the present invention, the starting diisocyanates and the diamines are continuously reacted in such quantity ratios which correspond to an equivalent ratio of isocyanate groups to amino groups of at least 8:1, preferably of 10:1 to 20:1, wherein the amino groups are entered in the calculation as monofunctional groups.

The essential feature of the invention is that the starting materials are reacted together at temperatures of above 180° C., preferably of above 200° C., immediately after they have been thoroughly mixed. These elevated reaction temperatures at the beginning of the reaction according to the present invention may be achieved by preheating the diisocyanate to temperatures of above 1 80° C., preferably above 200° C. The diamines used are conventionally used at temperatures of >100° C. in order to keep them in the liquid state. It may generally be assumed that, due to the elevated heat tonality, the temperature of the reaction mixture will rise within a few seconds to a temperature of 20–70° C. above the starting temperature.

Heating of the diisocyanates, which is required in every case, must be performed within the shortest possible period of time due to the known temperature sensitivity of these compounds, preferably within a period of time of less than 30 seconds. This is achieved by using appropriate prior art heat exchange units. The heat exchangers may be, for example, of the tube, bundle or plate design. They may be operated with a liquid heating medium, with pressurized steam or with direct electrical heating. It is particularly preferred to use heat exchangers which are capable of heating the starting diisocyanates within a period of time of less than 10 seconds.

After the described preheating, the continuous streams of the reaction partners are combined in a mixing chamber. The process according to the present invention places no particular requirements on the efficiency of the mixing chamber with regard to thorough mixing of the components.

The inlet orifices for the components into the mixing chamber are preferably in the form of nozzles, so that feeding may be performed under excess pressure. It may thus be ensured that the reaction mixture cannot enter the diisocyanate and diamine feed lines. To this end, the cross-sections are selected such that a pressure of 1.5 to 100 bar, preferably 1.5 to 40 bar, is established in each of the feed lines. The shape and arrangement of the nozzles and elevated pressure are not essential features of the invention since no particularly severe requirements are placed upon mixing performance. In contrast, care must be taken to ensure that the geometry of the mixing chamber is such that material is conveyed through the mixing chamber as far as possible without back-flow in order to prevent local excess concentrations of the amine and thus, the formation of solid polyureas. FIG. 1 shows the basic design.

The volume of the mixing chamber and of the downstream residence time section, which is optionally already cooled, and the intensity of the cooling in the downstream residence time section, must be selected such that the average residence time of the reaction mixture from when the starting components are combined until the temperature falls below 250° C. is at most 60 seconds, preferably at most 30 seconds and particularly preferably at most 10 seconds. In this manner, the average residence time of the reaction mixture at the preferred temperatures of above 270° C. is generally at most 20 seconds, preferably at most 10 seconds and particularly preferably, at most 1 second.

Once it has passed through the mixing chamber and the optional residence time section downstream from the mixing chamber, the reaction mixture is continuously cooled by suitable heat exchangers within at most 10 minutes, preferably at most 5 minutes, steadily or stepwise to a temperature within the temperature range from 120 to 200° C., preferably from 140 to 160° C. The essential feature in this connection is primarily that the reaction mixture is only exposed to the temperatures of above 250° C. for the above-stated short periods, wherein the duration of thermal post-treatment may vary within broad limits. In general, if low temperatures prevail in the last-stated zones, comparatively long thermal post-treatment is required, while at elevated temperatures, comparatively short thermal post-treatment is required. The temperature is then reduced as rapidly as possible to <50° C. by means of a high efficiency cooler in order to suppress the dimerization occurring as a secondary reaction which would otherwise result in the unwanted formation of solids.

The polyisocyanates containing biuret groups produced using the process according to the present invention are valuable starting materials for the production of two-component polyurethane plastics.

Figure 2:
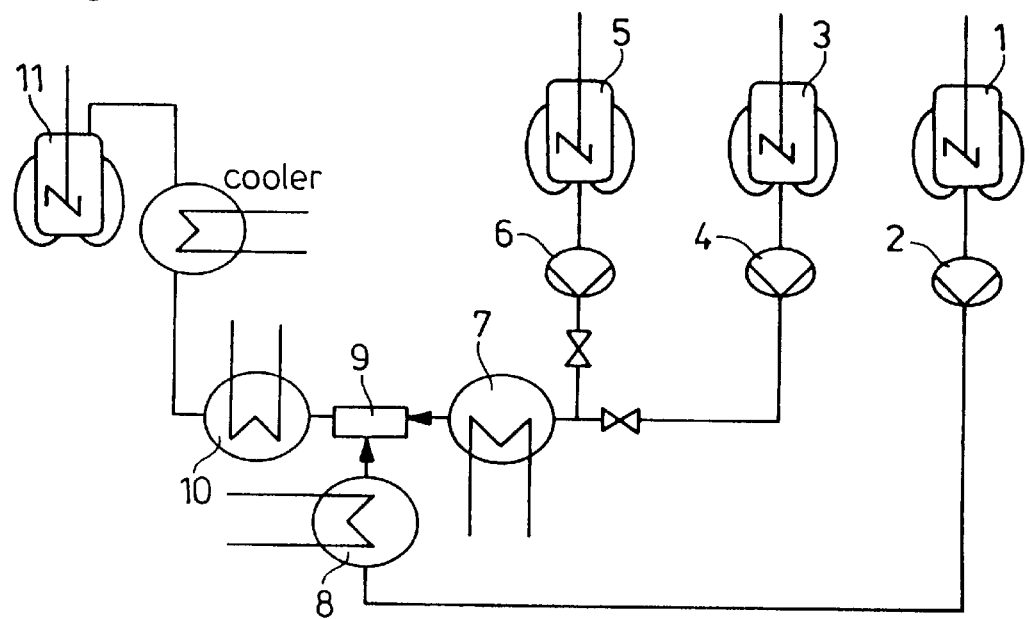
FIG. 2. An apparatus for the performance of the process according to the present invention.

In FIG. 2, wherein an apparatus of the present invention is shown, (1) means a stirred vessel for diisocyanate, (2) means a feed pump for diisocyanate, (3) means a stirred vessel for diamine, (4) means a feed pump for diamine, (5) means a stirred vessel for auxiliary solvent, (6) means a feed pump for auxiliary solvent, (7) means a heat exchanger for heating the diamine and auxiliary solvent, (8) means a heat exchanger for heating the diisocyanate, (9) means the mixing chamber, (10) means a heat exchanger for cooling the reaction mixture and (11) means a stirred vessel for the product of the process.

All percentages in the following Examples are weight percentages.

EXAMPLES

The apparatus disclosed in FIG. 2 was used in the following Examples. The auxiliary solvent (for example, xylene or ortho-dichlorobenzene from (5)) is used only initially for running in the continuously operated apparatus. The auxiliary solvent is passed into the mixing chamber (9) with the diisocyanate in order to establish constant temperature and pressure conditions in the mixing chamber (9), to ensure that no back-mixing of the components can occur in the feed lines. The actual start-up of the apparatus may be performed simply and safely by switching over from the solvent stream to the diamine stream. Nozzle-like restrictions are arranged upstream from the inlet into the mixing chamber of the diisocyanate and diamine lines in order to achieve elevated flow velocities at this point. The shape of these nozzles is, in principle, freely selectable since they do not have the task of imparting mixing energy to the reaction solution, provided that it is ensured that the material is conveyed without back-flow.

Immediately upon leaving the mixing chamber (9), the reaction mixture is cooled by a heat exchanger (10) to the lower temperature level within the residence times stated in the Examples. The reaction product is thermally post-treated in the stirred vessel (11) provided with a continuous feed and discharge, but could also proceed in a series of stirred-tank reactors or an appropriately sized residence time section.

Glass vessels are used as the stirred vessels (1), (3), (5) and (11), while metering piston pumps are used as the pumps (2), (4) and (6).

The heat exchangers (7) and (8) are double tube heat exchangers having the following dimensions and are operated countercurrently with oil or saturated steam as the heat transfer medium.

|  | (8) | (7) |
|---|---|---|
| Internal volume of heat exchanger | 22.8 cm$^3$ | 0.4 cm$^3$ |
| Heat exchange surface area | 415 cm$^2$ | 31.5 cm$^2$ |

The desired short residence times at elevated temperature can be achieved with these dimensions.

The mixing chamber (9) is in the form of a cylindrical tube with a nozzle orifice of 0.1 mm in diameter for the diamine and dimensions of 5 cm in length and a diameter of 2.5 mm. The heat exchanger (10) immediately downstream from the mixing chamber, is also a variable volume tube heat exchanger making it possible to adjust different sections to different temperatures. The precise conditions are listed separately in the individual Examples.

EXAMPLES 1 and 2

The reaction components are heated to the stated temperature in the heating heat exchangers with the flow rates stated in the Table and then reacted in the mixing chamber. Due to the heat tonality of the reaction, the temperature rose to the stated value.

The mixture is then purposefully cooled in the following heat exchangers to a final temperature of approx. 160° C. and then as fast as possible to a temperature of <50° C. Products having NCO contents of 42% and 37% and dynamic viscosities of 10–20 and 100–150 mPa.s at 25° C. are obtained.

The diisocyanate used was a mixture of 80 wt. % 2,4-tolylene disocyanate and 20 wt. % 2,6-tolylene diisocyanate (Desmodur T80®), wherein the diamine, which was used, was a corresponding isomeric mixture of tolylenediamines.

|  | Example 1 | Example 2 |
| --- | --- | --- |
| Diisocyanate: | | |
| Flow rate (kg/h) | 91.7 | 75.3 |
| Temperature after heating (° C.) | 202 | 204 |
| Diamine: | | |
| Flow rate (kg/h) | 3.26 | 5.00 |
| Temperature after heating (° C.) | 146 | 156 |
| Reaction Mixture: | | |
| Temperature after approx. 1 s (° C.) | 232 | 257 |
| Temperature after approx. 3 s (° C.) | 205 | 208 |
| Temperature after approx. 10 s (° C.) | 200 | 196 |
| Temperature after approx. 60 s (° C.) | 172 | 175 |
| Temperature after approx. 180 s (° C.) | 160 | 158 |
| Product: | | |
| NCO Content (%) | 42 | 37 |
| $\eta_{25° C.}$, mPa · s | 10–20 | 100–150 |

EXAMPLES 3 and 4

The reaction conditions are the same as described in example 1 and 2.

The diisocyanate used was diphenyl-4,4-diisocyanate. The diamine used was diaminodiphenylmethane.

EXAMPLE 5

The reaction conditions are the same as described in example 1 and 2.

The diisocyanate used was a mixture of 45 wt.-% diphenyl-4,4-diisocyanate and 55 wt.-% diphenyl-2,4-diisocyanate. The diamine used was diaminodiphenylmethane.

|  | Example 3 | Example 4 | Example 5 |
| --- | --- | --- | --- |
| Diisocyanate: | | | |
| Flow rate (kg/h) | 104.8 | 96.8 | 74.9 |
| Temperature after heating (° C.) | 200 | 205 | 203 |
| Diamine: | | | |
| Flow rate (kg/h) | 5.01 | 3.22 | 3.53 |
| Temperature after heating (° C.) | 145 | 150 | 148 |
| Reaction Mixture: | | | |
| Temperature after approx. 1 s (° C.) | 238 | 231 | 241 |
| Temperature after approx. 3 s (° C.) | 212 | 206 | 215 |
| Temperature after approx. 10 s (° C.) | 203 | 199 | 206 |
| Temperature after approx. 60 s (° C.) | 172 | 170 | 174 |
| Temperature after approx. 180 s (° C.) | 156 | 155 | 160 |
| Product: | | | |
| NCO Content (%) | 28 | 30.1 | 28.2 |
| $\eta_{25° C.}$, nPa.s | 220 | 59 | 117 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of polyisocyanates having a biuret structure, comprising:

a) continuously combining organic diisocyanates having aromatically attached isocyanate groups in a mixing chamber with organic diamines having aromatically attached amino groups in a molar ratio of at least 8:1 to form a reaction mixture, wherein said organic diamine is selected from a group consisting of 2,4-/2,6-tolylenediamine or diphenylmethanediamines; and b) reacting said reaction mixture at a temperature above 1 80° C., c) wherein a residence time of said reaction mixture in the mixing chamber from when said organic diisocyanates and said organic diamines are combined is at most 60 seconds.

2. A process according to claim 1, where said organic diisocyanates are combined with said organic diamines in said mixing chamber in a molar ratio of 10:1 to 20:1.

3. A process according to claim 1, wherein said organic diisocyanates are reacted with said organic diamines at a temperature in the range from 180 to 270° C.

4. A process according to claim 3, wherein said organic diisocyanates are reacted with said organic diamines at a temperature in the range from 200 to 270° C.

5. A process according to claim 1, wherein said organic diisocyanates having aromatically attached isocyanate groups is tolylene diisocyanate.

6. A process according to claim 1, wherein said organic diisocyanates having aromatically attached isocyanate groups is diphenylmethane diisocyanate.

7. A process according to claim 1, wherein said organic diamines having aromatically attached amino groups used are those having a molecular weight of below 300.

* * * * *